United States Patent [19]

Tinney et al.

[11] 4,035,348

[45] July 12, 1977

[54] TETRAPEPTIDES AND METHODS FOR THEIR PRODUCTION

[75] Inventors: Francis John Tinney; Ernest D. Nicolaides, both of Ann Arbor, Mich.

[73] Assignee: Parke, Davis & Company, Detroit, Mich.

[21] Appl. No.: 662,408

[22] Filed: Mar. 1, 1976

[51] Int. Cl.$^2$ .................................. C07C 103/52
[52] U.S. Cl. ............. 260/112.5 LH; 260/112.5 R; 424/177; 260/8
[58] Field of Search .......... 260/112.5 LH, 112.5 R, 260/8

[56] References Cited

U.S. PATENT DOCUMENTS 3,725,380  4/1973  Konig et al. ................ 260/112.5 R

OTHER PUBLICATIONS

J. M. Stewart and J. D. Young, "Solid Phase Peptide Synthesis", Freeman and Co., San Francisco, 1969, pp. 9–13.

J. D. Roberts and M. C. Caserio, "Basic Principles of Organic Chemistry", Benjamin, Inc., N.Y., 1965, pp. 531, 563–564.

E. Schroder and K. Lubke, "The Peptides", vol. 1, Academic Press, N.Y., 1965, pp. 79–80.

Primary Examiner—Delbert R. Phillips
Attorney, Agent, or Firm—Stephen Raines; George M. Richards; David B. Ehrlinger

[57] ABSTRACT

New tetrapeptides having the formula A-$R_1$-Tyr(benzyl)-Ser(benzyl)-D-Ala-$R_2$ wherein A is t-butoxycarbonyl, cyclohexylcarbonyl, benzyloxycarbonyl and p-nitrobenzyloxycarbonyl; $R_1$ is L-His(benzyl), D-Pro, or L-Trp; Tyr(benzyl) is D-Tyr-(benzyl) or L-Tyr(benzyl); Ser(benzyl) is D-ser(benzyl) or L-Ser(benzyl) and $R_2$ is lower alkoxy, hydrazino, amino, lower alkylamino or di(lower alkyl)amino.

6 Claims, No Drawings

TETRAPEPTIDES AND METHODS FOR THEIR PRODUCTION

SUMMARY AND DETAILED DESCRIPTION

The present invention relates to new peptide compounds that are useful as luteinizing hormone releasing factor antagonists and to methods for their production. More particularly, the invention relates to new N-protected tetrapeptides that are represented by the formula $$A-R_1-Tyr(benzyl)-Ser(benzyl)-D-Ala-R_2 \qquad I$$

wherein A is t-butoxycarbonyl, cyclohexylcarbonyl, benzyloxycarbonyl or p-nitrobenzyloxycarbonyl; $R_1$ is L-His(benzyl), D-Pro or L-Trp; Tyr(benzyl) is L-Tyr(benzyl) or D-Tyr(benzyl); Ser(benzyl) is L-Ser(benzyl) or D-Ser(benzyl) and $R_2$ is lower alkoxy, hydrazino, amino, lower alkylamino or di(lower alkyl) amino.

In formula I, the conventional symbols for amino acid residues of peptide compounds linked thereto are used and each is intended to have the following meaning: L-His(benzyl), $N^{im}$-benzyl-L-histidyl: D-Pro, D-prolyl; D-Ala, D-alanyl; L-Trp, L-tryptophyl; L-Tyr(benzyl), L-tyrosyl(benzyl); D-Tyr(benzyl), D-tyrosyl(benzyl), L-Ser(benzyl), L-seryl(benzyl) and D-Ser(benzyl), D-seryl(benzyl). In addition, the term "lower alkyl" is intended to mean a straight, branched or cyclic hydrocarbon moiety of up to six carbon atoms, such as methyl, ethyl, isopropyl and cyclopropyl and "lower alkoxy" is intended to mean an alkoxy group having a straight, branched or cyclic hydrocarbon moiety of up to 6 carbon atoms, such as methoxy, ethoxy and isopropoxy. These symbols and terms will also be used in the formulae that follow for other compounds and each such symbol or term should be understood to have the meaning given above.

In accordance with this invention, compounds of the formula I, wherein A and $R_1$ are as previously defined and $R_2$ is lower alkoxy, are produced by removing a protected tetrapeptide from a resin complex of the following structure $$A-R_1-Tyr(benzyl)-Ser(benzyl)-D-Ala-resin \qquad II$$

wherein said resin is a resin employed in solid phase peptide synthesis, such as those disclosed in a text by Stewart and Young, "Solid Phase Peptide Synthesis," W. H. Freeman & Company, San Francisco, 1969, which is incorporated by reference; preferably the resin is a crosslinked copolymer comprising 98 to 99 percent polystyrene crosslinked with 1 to 2 percent divinylbenzene, which is attached to the protected tetrapeptide through a methyleneoxy bridge wherein the methylene group is attached to the polymeric portion of the resin and the oxygen atom is attached to the protected tetrapeptide and A and $R_1$ are as previously defined; by treating said resin of the formula II with a lower alkyl alcohol in the presence of tertiary amine, such as triethylamine or tripropylamine.

The resin complex is suspended in an excess of the lower alkyl alcohol, preferably methanol for periods of from about 10 hours to 4 days, preferably 16 to 24 hours, at about 15° to about 35° C.

While a large excess of the lower alkyl alcohol is preferred, only a catalytic amount of tertiary amine is required; however, larger amounts are preferred, such as about 10 percent volume/volume based on the amount of lower alkyl alcohol employed.

While it is not a preferred procedure, compounds of the formula I wherein $R_2$ is hydrazino, amino, lower alkylamino or di(lower alkyl)amino may be prepared by reacting compounds of the formula II wherein A and $R_1$ are as previously defined, with hydrazine, ammonia, lower alkylamine or di(lower alkyl)amine.

The resin complex is suspended in a solvent, such as methanol, ethanol, dimethylformamide, etc., at a temperature of from about 0° to 50° C. for periods of from 12 hours to 10 days. When employing less reactive amines, the preferred solvent is dimethylformamide.

The complex resins of the formula are prepared by coupling a protected amino acid of the formula $$A-R_1-CH \qquad III$$

wherein A and $R_1$ are as previously defined, with complex resins of the formula $$Tyr(benzyl)-Ser(benzyl)-D-Ala-resin \qquad IV$$

in an organic solvent, such as dichloromethane with the aid of dicyclohexylcarbodiimide. The three reactants may be used in about equimolar quantities, but excess amounts of the protected amino acid and dicyclohexylcarbodiimide are sometimes advantageous. The reaction is generally conducted at about room temperature for a period of from about fifteen minutes to about 20 hours.

The complex resins of the formula IV are prepared by treating complex resins of the formula $$\text{t-butoxycarbonyl-Tyr(benzyl)-Ser(benzyl)-D-Ala-resin} \qquad V$$

with a large excess of trifluoroacetic acid utilizing dichloromethane as the solvent at temperatures of from 20° C. to 30° C. for about 10 minutes, followed by neutralization of the trifluoroacetic acid salt with a base such as triethylamine.

The complex resins of formula V are prepared by coupling $$\text{t-butoxycarbonyl-Tyr(benzyl)-OH}$$

to complex resins of the formula $$\text{Ser(benzyl)-D-Ala-resin}$$

using the reaction procedure described for the preparation of compounds of the formula II.

The complex resins of the formula VI are prepared by treating the complex resins of the formula $$\text{t-butoxycarbonyl-Ser(benzyl)-D-Ala-resin}$$

with trifluoroacetic acid using the reaction procedure for the preparation of compounds of the formula IV.

The complex resins of the formula VII are prepared by coupling $$\text{t-butoxycarbonyl-Ser(benzyl)-OH}$$

to complex resins of the formula $$\text{D-Ala-resin}$$

according to the procedure used for the preparation of compounds of formula II.

The complex resins of the formula VIII are prepared by treating the complex resins of the formula t-butoxycarbonyl-D-Ala-resin with trifluoroacetic acid using the reaction procedure for the preparation of compounds of the formula IV.

In accordance with this invention, compounds of the formula I, wherein A and $R_1$ are as previously described and $R_2$ is hydrazino, amino, lower alkylamino or di(lower alkyl)amino are prepared by reacting a compound of the formula I wherein $R_2$ is alkoxy, preferably methoxy, with hydrazine, ammonia, lower alkylamine or di(lower alkylamine).

The reactions are conducted at temperatures of from about 5° C. to 100° C. for from 3 hours to 4 days, preferably about room temperature. Generally, a large exccess of hydrazine, preferably used in the form of its hydrate, or amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

In addition, in accordance with this invention, compounds of the formula I, wherein A and $R_1$ are as previously defined and $R_2$ is amino, lower alkylamino or di(lower alkyl)amino are prepared by reacting a compound of the formula A-$R_1$-Tyr(benzyl)-Ser(benzyl)-D-Ala-$N_3$ with ammonia, lower alkylamine or di(lower alkyl)amine in a non-reactive solvent such as dimethylformamide, dioxane, tetrahydrofuran or mixtures thereof. The reaction is carried out at about −30° C. to 0° C. for about 12 to 24 hours, preferably −20° C. to 0° C. for from 16 to 19 hours. The two reactants are used in approximately equimolar amounts although a slight excess of the amine, about 10 percent, is preferred. When A is t-butoxycarbonyl, care should be taken to avoid the presence of a large excess of acid.

The azide compounds of the formula IX are normally prepared in situ by reacting a peptide hydrazide compound of the formula I wherein A and $R_1$ are as previously defined and $R_2$ is hydrazino, with a lower alkyl nitrite, preferably isoamyl nitrite in the presence of an acid, preferably hydrochloric acid, in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula I. The preparation of the azide is carried out at a temperature between −30° C. and 0° C. Following the in situ formation of the azide of formula IX and prior to the further reaction of the peptide azide with the appropriate amine to form certain tetrapeptides of formula I, a tertiary amine such as triethylamine is added to the reaction mixture to neutralize the acid used.

Compounds of the formula I wherein A and $R_1$ are as previously described and $R_2$ is hydrazino, amino, lower alkylamino or di(lower alkyl)amino are prepared by coupling a compound of the formula A-$R_1$-Tyr(benzyl)-Ser(benzyl)-D-Ala-OH with hydrazine, ammonia, a lower alkylamine or a di(lower alkyl)amine in an inert solvent in the presence of dicyclohexylcarbodiimide.

The above reaction is carried out using approximately equivalent amounts of reactants in a solvent such as dichloromethane, chloroform, tetrahydrofuran, dioxane or dimethylformamide, or mixtures thereof. The preferred solvent is tetrahydrofuran.

The temperature range for carrying out the reaction may be from 5° to 50° C., preferably room temperature for periods of from 10 hours to 5 days.

1-Hydroxybenzotriazole may also be used in the above reaction in addition to the dicyclohexylcarbodiimide. The 1-hydroxybenzotriazole is added in a ratio of one to two equivalents when compared to the reactants.

The compounds of the formula X are prepared by the hydrolysis of a compound of formula I wherein A and $R_1$ are as previously defined and $R_2$ is lower alkoxy. The reaction is conducted at temperatures of from 20° to 30° C. using about 0.5 ml. of the two normal aqueous sodium hydroxide solution and 10 ml. of solvent, usually water or an alcohol such as methanol, for each millimole of ester. The compound of formula X is isolated after acidification with aqueous citric acid.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

Tetrapeptides of this invention were screened for LRF antagonist activity in vitro using rat anterior pituitary cell cultures as described by Vale et al. [Endocrinology, 91, 562 (1972)]. The inhibition of LRF (luteinizing hormone release factor) induced luteinizing hormone (LH) release into the culture medium is the endpoint in this in vitro bioassay.

Following are the results of the above tests on certain preferred compounds.

| | ACTIVITY TABLE FOR IN VITRO TEST IN RAT ANTERIOR PITUITARY CELL CULTURES | | |
|---|---|---|---|
| | Molar Conc. | LH Value ng/ml. | % LH Release Inhibition |
| $N^\alpha$-t-butoxycarbonyl-$N^{1m}$-benzyl-L-histidyl-O-benzyl-L-tyrosyl-O-benzyl-L-seryl-D-alanine methyl ester | 1 × 10⁻⁶ | 21.15 | 73 |
| LRF Control | 1 × 10⁻⁹ | 60.76 | |
| Saline Control | | 6.54 | |
| $N^\alpha$-cyclohexylcarbonyl-$N^{1m}$-benzyl-L-histidyl-O-benzyl-L-tyrosyl-O-benzyl-L-seryl-D- | 1 × 10⁻⁸ | 28.70 | 59 |

-continued

ACTIVITY TABLE FOR IN VITRO TEST
IN RAT ANTERIOR PITUITARY
CELL CULTURES

|  | Molar Conc. | LH Value ng/ml. | % LH Release Inhibition |
|---|---|---|---|
| alanine methyl ester |  |  |  |
| LFR Control | $1 \times 10^{-9}$ | 60.76 |  |
| Saline Control |  | 6.54 |  |
| $N^\alpha$-t-butoxycarbonyl-D-prolyl-O-benzyl-L-tyrosyl-O-benzyl-L-seryl-D-alanine methyl ester | $1 \times 10^{-6}$ | 17.93 | 64 |
| LRF Control | $1 \times 10^{-9}$ | 38.98 |  |
| Saline Control |  | 6.25 |  |

The luteinizing hormone releasing factor is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH-RH, and its biological activity, see Science, Vol. 174, No. 4008, Oct. 29, 1971, pages 511–512. Thus, the tetrapeptides of this invention are useful in controlling ovulation and in restricting fertility.

The invention is illustrated by the following examples.

EXAMPLE 1

$N^\alpha$-Cyclohexylcarbonyl-L-tryptophyl-O-benzyl-L-tyrosyl-O-benzyl-L-seryl-D-alanine methyl ester $N^\alpha$-Cyclohexylcarbonyl-L-tryptophyl-O-benzyl-L-tyrosyl-O-benzyl-L-seryl-O-alanine resin, 5.4 g., is stirred with 60 ml. of triethylamine in 600 ml. of methanol overnight. The mixture is filtered and the solvent evaporated to yield 1.6 g., m.p. 225°–227° C. An additional quantity is obtained by extracting the resin with dimethylformamide.

$N^\alpha$-Cyclohexylcarbonyl-L-tryptophyl-O-benzyl-L-tyrosyl-O-benzyl-L-seryl-D-alanine resin is obtained from $N^\alpha$-t-butoxy-carbonyl-L-tryptophyl-O-benzyl-L-tyrosyl-O-benzyl-L-seryl-D alanine resin by de-protecting 7.1 g. with trifluoroacetic acid-dichloromethane (1:1, 200 ml.) during 10 to 15 minutes, liberating the amino compound with triethylamine and reacting it with 0.9 g., 7 mmol, of cyclohexanecarboxylic acid and 1.4 g., 7 mmol, of dicyclohexylcarbodiimide. The coupling reaction is rocked for 20 hours and the resin washed 2 times with dichloromethane. The resin is washed from the flask with three portions of methanol-chloroform (1:2) and successively washed three times with methanol and three times with ether. It is dried in air; 5.4 g.

The $N^\alpha$-t-butoxycarbonyl-L-tryptophyl-O-benzyl-L-tyrosyl-O-benzyl-L-seryl-D-alanine resin is obtained from 10 g., 0.0093 mol, of $N^\alpha$-t-butoxycarbonyl-D-alanine resin, according to the general procedure given below for preparing peptide resins, 1. using 4.2 g., 0.014 mol, of $N^\alpha$-t-butoxycarbonyl-O-benzyl-L-serine and 2.9 g., 0.014 mol, of dicyclohexylcarbodiimide, 2. 5.7 g., 0.014 mol, of $N^\alpha$-t-butoxycarbonyl-O-benzyl-L-tyrosine and 2.9 g., 0.014 mol of dicyclohexylcarbodiimide and 3. 4.3 g., 0.014 mol, of $N^\alpha$-t-butoxycarbonyl-L-tryptophan and 2.9 g., 0.014 mol, of dicyclohexylcarbodiimide.

$N^\alpha$-t-Butoxycarbonyl-D-alanine resin is obtained by mixing 4.0 g. of chloromethylated resin crosslinked with 1% divinylbenzene, 14 g. of $N^\alpha$-t-butoxycarbonyl-D-alanine and 7.4 g. of triethylamine in 500 ml. of ethanol at reflux for three days, filtered and washed with ethanol and ether. After drying, analysis shows 0.00092 mol of $N^\alpha$-t-butoxycarbonyl-D-alanine/gram.

General Procedure for the Solid Phase Synthesis of Peptide Resins

The peptide resin is obtained by attaching an α-amino protected amino acid to a resin (usually a chloromethylated resin which is commercially available from Lab Systems, Inc., San Mateo, Cal.) The peptide system is then constructed by de-protecting the α-amino-protected amino acid resin and attaching an α-amino-protected amino acid. Repetition of this process produces the peptide resin having the required number and sequence of the desired peptide. The terminal α-amino protection is changed by de-protection and attaching the desired carboxylic terminal group. The solid phase synthesis procedure is described by J. M. Stewart "Solid Phase Peptide Synthesis," W. H. Freeman and Co., 1969.

Each cycle of the procedure follows the scheme:

1. De-protection with excess 50% trifluoroacetic acid in dichloromethane.
2. Three washes with dichloromethane.
3. Neutralization of the trifluoroacetic acid salt with an excess of cold 10% triethylamine in dichloromethane.
4. Three washes with dichloromethane.
5. Fifteen to thirty minutes agitation with the α-amino-protected amino acid in 20% molar excess (based on the resin nitrogen analysis). In an alternate method, a 4-fold excess of the α-amino-protected amino acid is agitated with the resin for fifteen minutes and the excess recovered by draining the solution from the reactor.
6. Addition of dicyclohexylcarbodiimide at least equivalent to the α-amino-protected amino acid in Step 5 in dichloromethane followed by agitation for 4 to 20 hours. In the alternate method, a 3.3-fold excess of dicyclohexylcarbodiimide is used relative to the α-amino-protected amino acid resin.
7. Three washes with dichloromethane.

EXAMPLE 2

$N^\alpha$-Cyclohexylcarbonyl-L-tryptophyl-O-benzyl-L-tyrosyl-O-benzyl-L-seryl-D-alanine N-ethylamide $N^\alpha$-Cyclohexylcarbonyl-L-tryptophyl-O-benzyl-L-tyrosyl-O-benzyl-L-seryl-D-alanine methyl ester, 0.3 g., is dissolved in 50 ml. of methanol and 50 ml. of dimethylformamide, treated with 5 ml. of ethylamine and the reaction stirred at room temperature for 2 days. The solvent is removed by evaporation and the residue is chromatographed on silica gel using chloroform-methanol-water (60:30:5); m.p. 255°–260° C.

EXAMPLE 3

$N^\alpha$-t-Butoxycarbonyl-$N^{im}$-benzyl-L-histidyl-O-benzyl-L-tyrosyl-O-benzyl-L-seryl-D-alanine methyl ester $N^\alpha$-t-Butoxycarbonyl-$N^{im}$-benzyl-L-histidyl-O-benzyl-L-tyrosyl-O-benzyl-L-seryl-D-alanine resin, 9.0 g., is treated with methanol, 600 ml., and triethylamine, 60 ml., at room temperature for 2 days, filtered and the filtrate evaporated. The crude product is chromatographed on silica gel with chloroform-methanol-water (60:30:5) to give 3.1 g. as a hemihydrate; m.p. 62°–66° C.

The $N^\alpha$-t-butoxycarbonyl-$N^{im}$-benzyl-L-histidyl-O-benzyl-L-tyrosyl-O-benzyl-L-seryl-D-alanine resin is obtained by the general procedure of Example 1 using 20 g., 0.0132 mol, of $N^\alpha$-t-butoxycarbonyl-D-alanine resin with (1) 5.9 g., 0.02 mol, of $N^\alpha$-t-butoxycarbonyl-O-benzyl-L-serine and 4.1 g., 0.02 mol, of dicyclohexylcarbodiimide, (2) 7.4 g., 0.02 mol, of $N^\alpha$-t-butoxycarbonyl-O-benzyl-L-tyrosine and 4.1 g., 0.02 mol, of dicyclohexylcarbodiimide and (3) 6.9 g., 0.02 mol, of $N^\alpha$-t-butoxycarbonyl-$N^{im}$-benzyl-L-histidine and 4.1 g., 0.02 mol, of dicyclohexylcarbodiimide.

EXAMPLE 4

$N^\alpha$-t-Butoxycarbonyl-$N^{im}$-benzyl-L-histidyl-O-benzyl-L-tyrosyl-O-benzyl-L-seryl-D-alanine N-ethylamide The methyl ester from Example 3, 0.3 g., is reacted with 5 g. of ethylamine and 100 ml. of methanol at room temperature for 4 days. The product, 0.17 g., is obtained as a hemi-hydrate after evaporation and trituration with ether; m.p. 140°–144° C.

EXAMPLE 5

$N^\alpha$-t-Butoxycarbonyl-$N^{im}$-benzyl-L-histidyl-O-benzyl-L-tyrosyl-O-benzyl-L-seryl-D-alaninamide The methyl ester of Example 3, 0.3 g., is reacted with 100 ml. of methanol saturated with ammonia at room temperature for two days. After removal of the methanol and ammonia by evaporation, the crude product is chromatographed on silica gel using chloroform-methanol-water (60:30:5) to give 0.2 g. of the product as a hemi-hydrate; m.p. 144°–149° C.

EXAMPLE 6

$N^\alpha$-Cyclohexylcarbonyl-$N^{im}$-benzyl-L-histidyl-O-benzyl-L-tyrosyl-O-benzyl-L-seryl-D-alanine methyl ester $N^\alpha$-Cyclohexylcarbonyl-$N^{im}$-benzyl-L-histidyl-O-benzyl-L-tyrosyl-O-benzyl-L-seryl-D-alanine resin, 8.1 g., is treated with methanol, 600 ml., and triethylamine, 60 ml., for 24 hours. After filtration and evaporation, the crude product is an oil which is further purified by chromatography on silica gel with chloroform-methanol-water (60:30:5) to yield 2.4 g. as a hydrate; m.p. 140°–145° C.

$N^\alpha$-Cyclohexylcarbonyl-$N^{im}$-benzyl-L-histidyl-O-benzyl-L-tyrosyl-O-benzyl-L-seryl-D-alanine resin is obtained by treatment of 9 g. of $N^\alpha$-t-butoxycarbonyl-$N^{im}$-benzyl-L-histidyl-O-benzyl-L-tyrosyl-O-benzyl-L-seryl-D-alanine resin (Example 3) by the general procedure of Example 1 using 0.9 g., 0.007 mol, of cyclohexane carboxylic acid and 1.4 g., 0.007 mol, of dicyclohexylcarbodiimide.

EXAMPLE 7

$N^\alpha$-Cyclohexylcarbonyl-$N^{im}$-benzyl-L-histidyl-O-benzyl-L-tyrosyl-O-benzyl-L-seryl-D-alanine N-ethylamide The methyl ester of Example 6, 0.3 g., is treated with 5 g. of ethylamine in 100 ml. of methanol at room temperature for four days. The product is obtained by evaporation of the reaction mixture, repeated solution in ethanol and evaporation and finally, trituration of the solid with ether. The product, 0.15 g., is obtained as a monohydrate, m.p. 158°–162° C.

EXAMPLE 8

$N^\alpha$-Cyclohexylcarbonyl-$N^{im}$-benzyl-L-histidyl-O-benzyl-L-tyrosyl-O-benzyl-L-seryl-D-alaninamide The methyl ester of Example 6, 0.3 g., is treated with 100 ml. of methanol saturated with ammonia at room temperature for 2 days. After evaporation, the crude product is chromatographed on silica gel using chloroform-methanol-water (60:30:5) to yield 0.15 g. of the product as a monohydrate; m.p. 172°–176° C.

EXAMPLE 9

$N^\alpha$-t-Butoxycarbonyl-D-prolyl-O-benzyl-L-tyrosyl-O-benzyl-L-seryl-D-alanine methyl ester $N^\alpha$-t-Butoxycarbonyl-D-prolyl-O-benzyl-L-tyrosyl-O-benzyl-L-seryl-D-alanine resin is mixed with 100 ml. of methanol, 50 ml. of dimethylformamide and 20 ml. of triethylamine at room temperature for 3 days. After filtration, the crude product obtained by evaporation is an oil which is solidified by trituration with isopropanol and then crystallized from isopropanol to yield 1.0 g.; m.p. 157°–158° C.

$N^\alpha$-t-Butoxycarbonyl-D-prolyl-O-benzyl-L-tyrosyl-O-benzyl-L-seryl-D-alanine resin is obtained from $N^\alpha$-t-butoxycarbonyl-D-alanine resin, 10 g. 6.6 mmol, according to the general procedure of Example 1 using (1) 2.1 g. 6.9 mmol, of $N^\alpha$-t-butoxycarbonyl-O-benzyl-L-serine and 1.7 g., 8.2 mmol, of dicyclohexylcarbodiimide. (2) 3.2 g., 8.6 mmol, of $N^\alpha$-t-butoxycarbonyl-O-benzyl-L-tyrosine and 1.7 g., 8.2 mmol, of dicyclohexylcarbodiimide and (3) 1.8 g., 8.4 mmol, of $N^\alpha$-t-butoxycarbonyl-D-proline and 1.7 g., 8.2 mmol, of dicyclohexylcarbodiimide.

EXAMPLE 10

$N^\alpha$-t-Butoxycarbonyl-D-prolyl-O-benzyl-L-tyrosyl-O-benzyl-L-seryl-D-alanine N-ethylamide $N^\alpha$-t-Butoxycarbonyl-D-prolyl-O-benzyl-L-tyrosyl-O-benzyl-L-seryl-D-alanine methyl ester, 500 mg. is dissolved in 20 ml. of methanol and treated with 10 ml. of ethylamine. The solution is let stand at 25° C. for 3 days, is then filtered and the solvent evaporated. The residue solidifies on trituration with petroleum ether; 500 mg. as a hemi-hydrate; m.p. 155°–160° C.

EXAMPLE 11

N$^\alpha$ -Butoxycarbonyl-L-tryptophyl-O-benzyl-D-tyrosyl-O-benzyl-L-seryl-D-alanine methyl ester N$^\alpha$ -t-Butoxycarbonyl-L-tryptophyl-O-benzyl-D-tyrosyl-O-benzyl-L-seryl-D-alanine resin, 7.5 g., is mixed with 50 ml. of dimethylformamide, 150 ml. of methanol and 20 ml. of triethylamine at room temperature for 16 hours. The residue from evaporation of the solvents is triturated with ether and petroleum ether and then crystallized from isopropanol and petroleum ether to yield 1.68 g. as a hemi-hydrate; m.p. 160°–163° C.

N$^\alpha$ -t-Butoxycarbonyl-L-tryptophyl-O-benzyl-D-tyrosyl-O-benzyl-L-seryl-D-alanine resin is obtained according to the general procedure of Example 1 from 14 g., 7.3 mmol, of N$^\alpha$ -t-butoxycarbonyl-O-benzyl-D-tyrosyl-O-benzyl-L-seryl-D-alanine resin and 4.0 g., 13 mmol, of N$^\alpha$ -t-butoxycarbonyl-L-tryptophan and 2.7 g., 13 mmol, of dicyclohexylcarbodiimide. N$^\alpha$ -t-butoxy-carbonyl-O-benzyl-D-tyrosyl-O-benzyl-L-seryl-D-alanine resin is obtained according to the procedure of Example 1 from 40 g., 32 mmol, of N$^\alpha$ -t-butoxycarbonyl-D-alanine resin with (1) 10.7 g., 35 mmol, of N$^\alpha$ -t-butoxycarbonyl-O-benzyl-L-serine and 7.21 g., 35 mmol, of dicyclohexylcarbodiimide and (2) with 20 g. 11 mmol, of the N$^\alpha$ -t-butoxycarbonyl-O-benzyl-L-seryl-D-alanine resin 7.0 g., 19 mmol, of N$^\alpha$ -t-butoxycarbonyl-O-benzyl-D-tyrosine and 3.9 g., 19 mmol, of dicyclohexylcarbodiimide.

EXAMPLE 12

N$^\alpha$ -t-Butoxycarbonyl-L-tryptophyl-O-benzyl-D-tyrosyl-O-benzyl-L-seryl-D-alanine N-ethylamide

N$^\alpha$ -t-Butoxycarbonyl-L-tryptophyl-O-benzyl-D-tyrosyl-O-benzyl-L-seryl-D-alanine methyl ester, 700 mg., is dissolved in 30 ml. of dimethylformamide and treated with 10 ml. of ethylamine. The solution is let stand for 6 days, filtered and evaporated. The residue is crystallized from isopropanol and petroleum ether to yield 430 mg.; $[\alpha]_D^{23}$ –2° (c. 0.79, DMF).

EXAMPLE 13

N$^\alpha$ -t-Butoxycarbonyl-L-tryptophyl-O-benzyl-L-tyrosyl-O-benzyl-L-seryl-D-alanine methyl ester N$^\alpha$ -t-Butoxycarbonyl-L-tryptophyl-O-benzyl-L-tyrosyl-O-benzyl-L-seryl-D-alanine resin, 7.1 g., prepared in Example 1 is mixed with methanol, 600 ml., and triethylamine, 60 ml., at room temperature for 2 days. After filtration and evaporation, the crude product, 2.7 g., is chromatographed on silica gel with chloroform-methanol-water (60:30:5) to yield 1.9 g., m.p. 178°–182° C.

EXAMPLE 14

N$^\alpha$ -t-Butoxycarbonyl-L-tryptophyl-O-benzyl-L-tyrosyl-O-benzyl-L-seryl-D-alanyl hydrazide The methyl ester of Example 13, 0.4 g., is reacted with 1 g. of hydrazine hydrate in 150 ml. of methanol at room temperature for two days. After evaporation, the crude product is chromatographed on silica gel with chloroform-methanol-water (60:30:5) to give 0.31 g. of the product as a hemi-hydrate, m.p. 205°–210° C.

EXAMPLE 15

N$^\alpha$ -t-Butoxycarbonyl-L-tryptophyl-O-benzyl-L-tyrosyl-O-benzyl-L-seryl-D-alanine N-ethylamide The methyl ester of Example 13, 0.4 g., is mixed with 5 g. of ethylamine in 100 ml. of methanol at room temperature for 4 days. The product, obtained by evaporation, is twice dissolved in methanol and recovered by evaporation. It is then triturated with ether to yield the product as a quarter-hydrate, 0.23 g., m.p. 215°–220° C.

EXAMPLE 16

N$^\alpha$ -Benzyloxycarbonyl-L-tryptophyl-O-benzyl-D-tyrosyl-O-benzyl-L-seryl-D-alanine methyl ester N$^\alpha$ -t-Butoxycarbonyl-O-benzyl-O-tyrosyl-O-benzyl-L-seryl-D-alanine resin (Example 11), 6.4 g., 5.1 mmol, is coupled with 2.23 g., 6.3 mmol, of N$^\alpha$ -benzyloxycarbonyl-L-tryptophan and 1.3 g., 6.3 mmol, of dicyclohexylcarbodiimide according to the general procedure of Example 1. The resulting N$^\alpha$ -benzyloxy-carbonyl-L-tryptophyl-O-benzyl-D-tyrosyl-O-benzyl-L-seryl-D-alanine resin is mixed with 20 ml. of triethylamine, 150 ml. of methanol and 50 ml. of dimethylformamide and let stand overnight. After filtration and evaporation, the crude product is triturated with either-petroleum ether and crystallized from isopropanol; 1.75 g.; $[\alpha]_D^{23}$ –5° (c. 1.01, DMF).

EXAMPLE 17

N$^\alpha$ -Benzyloxycarbonyl-L-tryptophyl-O-benzyl-D-tyrosyl-O-benzyl-L-seryl-D-alanine N-ethylamide N$^\alpha$ -Benzyloxycarbonyl-L-tryptophyl-O-benzyl-D-tyrosyl-O-benzyl-L-seryl-D-alanine methyl ester, 650 mg., is dissolved in 30 ml. of dimethylformamide and treated with 10 ml. of ethylamine. The solution is let stand for seven days, filtered and the filtrate evaporated. The product is crystallized from isopropanol to yield 380 mg.; $[\alpha]_D^{23}$ –7° (c. 1.03, DMF).

EXAMPLE 18

N$^\alpha$ -t-Butoxycarbonyl-N$^{im}$-benzyl-L-histidyl-O-benzyl-L-tyrosyl-O-benzyl-L-seryl-D-alanyl hydrazide The methyl ester of Example 3, 0.3 g., is reacted with 1 g. of hydrazine hydrate in 150 ml. of methanol. After removal of the solvent, the crude product is chromatographed on silica gel using chloroform-methanol-water (60:30:5) to give 0.13 g. of the product melting at 146°–150° C.

We claim

1. A tetrapeptide represented by the formula

A-R$_1$-Tyr(benzyl)-Ser(benzyl)-D-Ala-R$_2$ wherein A IS t-butoxycarbonyl, cyclohexyl-carbonyl, benzyloxycarbonyl or p-nitrobenzyloxycarbonyl; R$_1$ is L-His(benzyl), D-Pro, or L-Trp; Tyr(benzyl) is L-Tyr(benzyl) or D-Tyr(benzyl); Ser(benzyl) is L-Ser(benzyl) or D-Ser(benzyl) and R$_2$ is lower alkoxy, hydrazino, amino, lower alkylamino or di(lower alkyl)amino.

2. The compound of claim 1 having the name N$^\alpha$ -t-butoxycarbonyl-N$^{im}$-benzyl-L-histidyl-O-benzyl-L-tyrosyl-O-benzyl-L-seryl-D-alanine methyl ester.

3. The compound of claim 1 having the name N$^\alpha$ -t-butoxycarbonyl-N$^{im}$-benzyl-L-histidyl-O-benzyl-L-tyrosyl-O-benzyl-L-seryl-D-alaninamide.

4. The compound of claim 1 having the name N$^\alpha$ -cyclohexylcarbonyl-N$^{im}$-benzyl-L-histidyl-O-benzyl-L-tyrosyl-O-benzyl-L-seryl-D-alanine methyl ester.

5. The compound of claim 1 having the name N$^\alpha$ -t-butoxycarbonyl-D-prolyl-O-benzyl-L-tyrosyl-O-benzyl-L-seryl-D-alanine methyl ester.

6. The compound of claim 1 having the name N$^\alpha$ -t-butoxycarbonyl-L-tryptophyl-O-benzyl-L-tyrosyl-O-benzyl-L-seryl-D-alanine methyl ester.

* * * * *